(12) United States Patent
Deshpande et al.

(10) Patent No.: US 6,881,837 B2
(45) Date of Patent: Apr. 19, 2005

(54) CHEMICAL SYNTHESIS OF S-ADENOSYL-L-METHIONINE WITH ENRICHMENT OF (S,S)-ISOMER

(75) Inventors: Pandurang Balwant Deshpande, Tamilnadu (IN); Udayampalam Palanisamy Senthilkumar, Tamilnadu (IN); Ramar Padmanabhan, Tamilnadu (IN)

(73) Assignee: Orchid Chemicals & Pharmaceuticals Ltd., Tamil Nadu (IN)

( * ) Notice: Subject to any disclaimer, the term of this patent is extended or adjusted under 35 U.S.C. 154(b) by 549 days.

(21) Appl. No.: 09/875,044

(22) Filed: Jun. 7, 2001

(65) Prior Publication Data

US 2002/0188116 A1 Dec. 12, 2002

(51) Int. Cl.$^7$ .............................................. C07H 19/04
(52) U.S. Cl. ..................................... 536/27.31; 536/127
(58) Field of Search ............................ 536/27.31, 124

(56) References Cited

FOREIGN PATENT DOCUMENTS

| | | |
|---|---|---|
| CA | 1057681 | 7/1979 |
| DE | 2530898 | 1/1976 |
| JP | 48044491 | 6/1973 |
| JP | 50082288 | 7/1975 |
| JP | 53005399 | 1/1978 |
| JP | 54154774 | 12/1979 |
| JP | 56099499 | 8/1981 |
| JP | 57086297 | 5/1982 |
| JP | 57086298 | 5/1982 |
| JP | 57099199 | 6/1982 |
| JP | 58036397 | 3/1983 |
| JP | 60070097 | 4/1985 |
| RO | 63045 | 6/1978 |

OTHER PUBLICATIONS

Matos, J. et al "S–Adenosylmethionine: Studies on Chemical and Enzymatic Synthesis" Biotechnol. Appl. Biochem. vol. 9, pp. 39–52, 1987.*

Ramalingam, K. "Preparation of S–(N,N–dimethyladenosyl)–L–methionine" Carbohyd. Res. vol. 142, pp. 123–126, 1985.*

* cited by examiner

Primary Examiner—James O. Wilson
Assistant Examiner—Leigh C. Maier
(74) Attorney, Agent, or Firm—Burns, Doane, Swecker & Mathis, L.L.P.

(57) ABSTRACT

This invention relates to the production of S-adenosyl-L-methionine by means of a chemical process wherein enrichment of the bioactive (S,S)-isomer is achieved. The process is simple, efficient, economical and reproducible on large scale.

16 Claims, 3 Drawing Sheets

CHEMICAL SYNTHESIS OF S-ADENOSYL-L-METHIONINE WITH ENRICHMENT OF (S,S)-ISOMER

FIELD OF THE INVENTION

This invention relates to a first-ever chemical process for the industrial manufacture of S-adenosyl-L-methionine, which consists of diastereoselective methylation of S-adenosyl-L-homocysteine with the enrichment of active (S,S)-isomer.

BACKGROUND OF THE INVENTION

S-Adenosyl-L-methionine, known as SAMe, is the main biological donor of methyl groups and it has several important therapeutic applications. As a substance existing in the living body, SAMe has been found to possess various pharmacological actions such as improvement of energy state of ischemic brain, improvement of cerebral energy metabolism and acidosis of the model with recirculated blood flow following ischemia, etc. Variety of other functions such as inhibition of neuronal death following ischemia, improvement of cerebral glucose utility, inhibition of brain edema, improvement of EEG, improvement of evoked potential, amebiorative action on motor function, and therefore reported to be important as a cure for stroke. SAMe as an antioxidant, use for osteoarthritis, liver protection and to control aging in elderly people is also suggested.

SAMe is an important molecule in normal cell function and its survival. SAMe is utilized by three key metabolic pathways: trans-methylation, trans-sulfuration and polyamine synthesis. In transmethylation reactions, the methyl group of SAMe is donated to a large variety of acceptor substrates including DNA, phospholipids and proteins. In trans-sulfuration, the sulfuration of SAMe is converted via a series of enzymic steps to cysteine, a precursor of taurine and glutathione, a major cellular anti-oxidant. Given the importance of SAMe in tissue function, it is not surprising that this molecule is being investigated as a possible therapeutic agent for the treatment of various clinical disorders as mentioned in *Int. J. Biochem. Cell Biol.* (2000), 32(4), 391–395.

BRIEF DESCRIPTION OF THE DRAWING FIGURES

PRIOR ART

There are numerous methods known to prepare SAMe at various scales and all are enzymatic and fermentation based. JP 58036397, JP 60070097, JP 56099499 and JP 54154774 describe the preparation of S-adenosyl-L-methionine using yeast. In this process the yeast extract was adsorbed on the resin and SAMe was eluted using suitable acids. The dilute solution of the product is concentrated using reverse osmosis and the product was isolated by spray-drying. Alternatively in RO 63045, CA 1057681 and DE 2530898, use of picrolinic acid was suggested for the product isolation from the fermented mass.

Use of *Saccharomyces* cultured on methionine media, cells of *Rhizopus pseudochinesis* cultured in a medium containing methionine and the use of different cultures of various origin are reported in JP 48044491, JP 47037038, JP 53005399, and JP 50082288. Microbial production of S-adenosyl-L-methionine by reacting adenosine triphosphate (ATP) and methionine catalyzed by enzyme from yeast or other fungi and the *Lactobacillus bulgaricus* containing the yeast extract are described in JP 57099199, JP 57086297 and JP 57086298.

Figure 1:
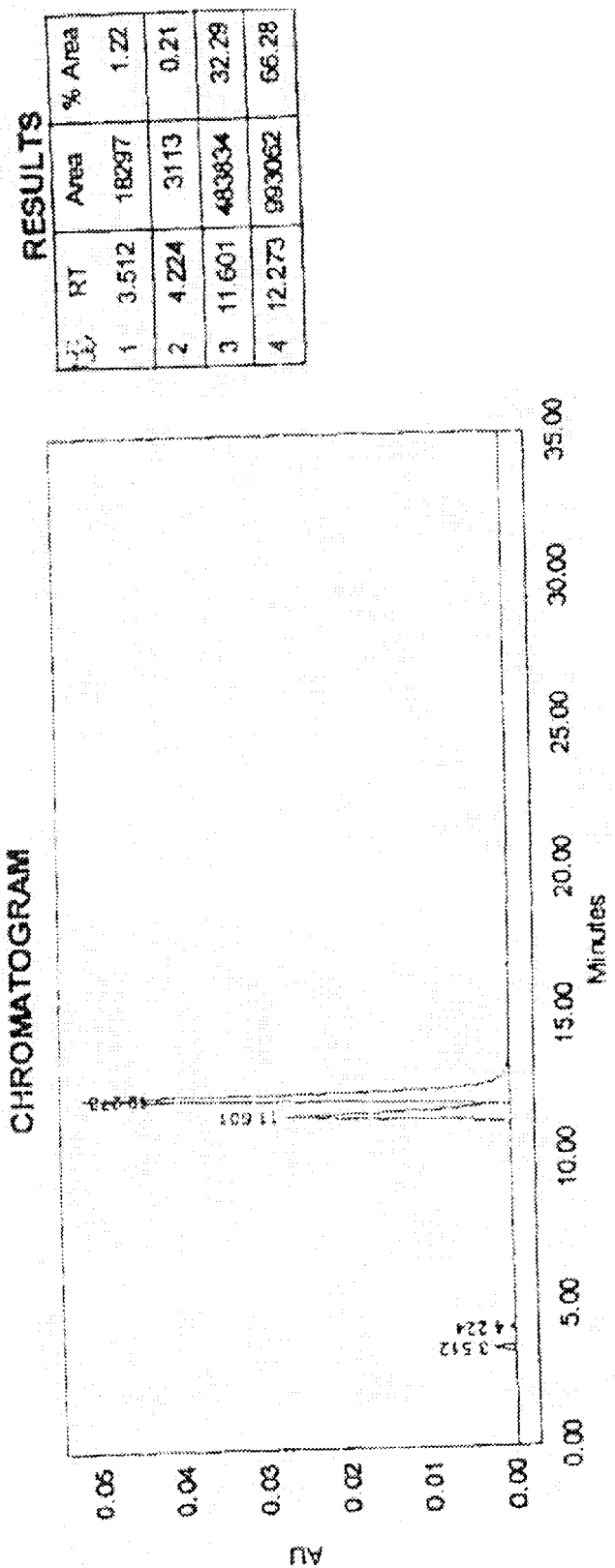
FIG. 1 is a chromatogram showing peaks of (S,S) and (R,S) isomes of SAMe, SAMe is produced by the prior art process here.

In all the above methods, enrichment of (S,S)-isomer of SAMe has been achieved; however, it is not exclusive. Normally, i.e., it in produced with other substitutes percentage observed for the (S,S)-isomer in the SAMe samples analyzed by HPLC method was ranging from 60% to 75% as shown in FIG. 1 wherein the first peak corresponds to (R,S)-isomer and the second peak, (S,S)-isomer. The varying isomer ratios are attributed to the method of product isolation and the temperature at which the enzyme reaction is effected.

All the above methods have several limitations with respect to the productivity per day and require high investment. Some of the problems associated with these methods are as under:

1. Isolation of required enzyme from its natural sources is difficult and for few milligrams of enzyme a large quantity of cells are required.

2. Enzymatic synthesis of SAMe indicated the problem of product inhibition. The 5 and 10 mM reactions do not even form 1 mM of SAMe. The same is the case with immobilized enzymes. Thus, in enzymatic synthesis, non-competitive product inhibition of SAMe vs methionine leads to decrease in the rate of SAMe production at high concentration as reported in the *Biotechnol. Appl. Biochem.* (1987), 9(1), 39–52.

3. The product isolation is tedious and various techniques like ultra-filtration with molecular cut off, ion exchange resins columns and reverse osmosis need to be used. Thus, it requires high investment to adopt the above methods, apart from the limitations due to heavy reactor occupancy and very high dilution involved during downstream processing.

Figure 2:
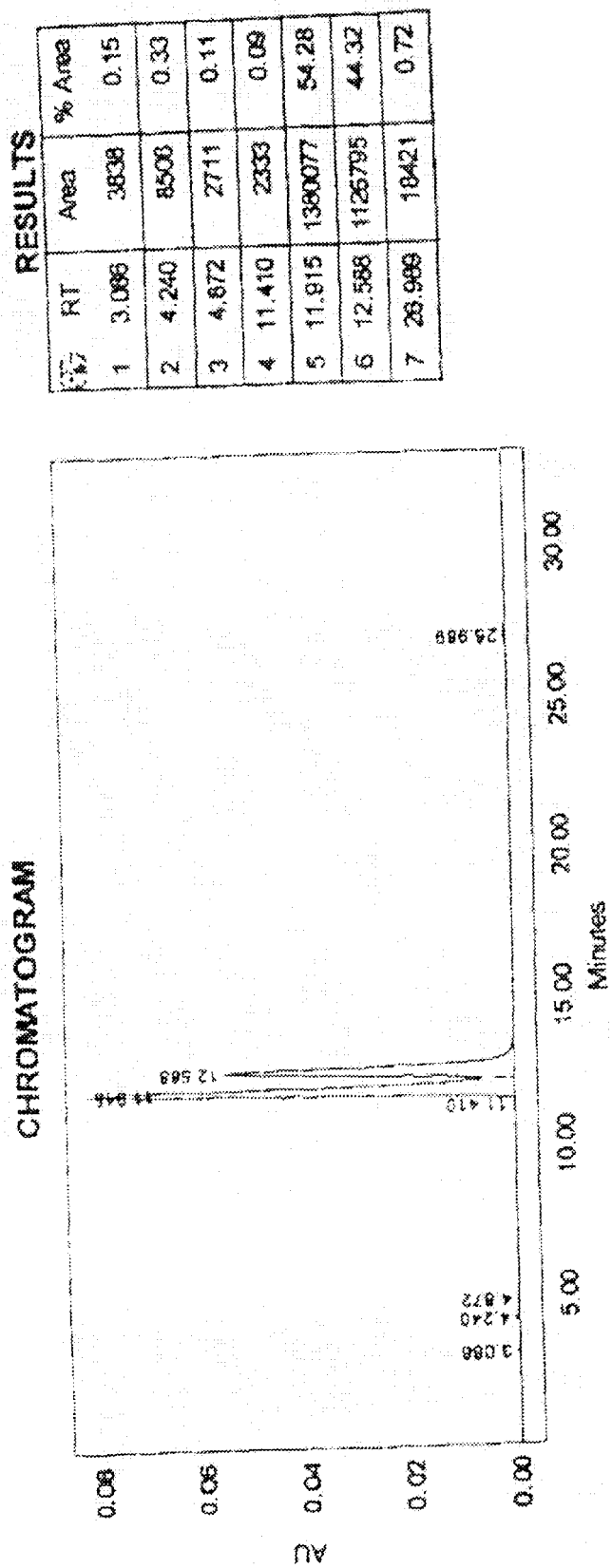
FIG. 2 is a chromatogram showing production of isomers of SAMe by chemical route.

Thus the prior art teaches the production of SAMe by fermentation. While there are a few stray attempts to synthesize SAMe chemically, they have met with little success for manufacture of SAMe on commercial scale. The reason being that chemical method does not normally give the required minimum enrichment of (S,S)-isomer as shown in FIG. 2 wherein (R,S)-isomer is 55–65% and the required (S,S)-isomer is 35–45%. The available methods produce a lot of side products owing to the presence of multiple centers in S-adenosyl-L-homocysteine susceptible to methylation.

A report by Jose R. Matos et al. published in the *Biotechnol. Appl. Biochem.* (1987), 9(1), 39–52 reveals the use of methyl iodide and trimethylsulfonium iodide (TMSI) for methylation of S-adenosyl-L-homocysteine and reports the formation of inactive isomer as a major product in a 60:40 [(R,S)-isomer: (S,S)-isomer] mole ratio. The reaction of methyl iodide was performed in 85% formic acid and was kept in dark for 3–5 days to complete. The product was isolated using Amberlite IRC-50 resin columns and lyophilized. The methylation reaction with TMSI has the disadvantage of demethylation as the concentration of dimethyl sulfide is increased in the reaction. At certain stage, reaction attains equilibrium and the formation of side product predominates. Both the methods are not useful for large scale manufacture due to its asymmetrically non-specific approach, longer reaction time, formation of side products and low yields of the required isomer. In addition, the quantum of the required isomer is much less than that obtained by the fermentation methods.

Thus, there is a need in the prior art to develop a chemical method for methylation of S-adenosylhomocysteine which should be high yielding, reproducible on larger scale with the predominance of the active (S, S)-isomer and minimum impurities.

OBJECTS OF THE INVENTION

The main object of the invention is to develop a chemical method for large scale manufacturing of S-adenosyl-L-homocysteine (SAH) from adenosine and L-methionine as well as to develop a chemical approach for the stereoselective methylation of SAH, preferably, with a different methylating agent.

Another objective of the present invention is to improve the process for the production of SAMe which is commercially viable and applicable to large scale operations.

Yet another objective is to methylate S-adenosyl-L-homocysteine to obtain SAMe with enrichment of required (S,S)-isomer.

Still another objective of the present invention is to develop an industrially feasible technique for the isolation of S-adenosyl-L-methionine from the aqueous medium after the methylation of SAH wherein the use of ultrafiltration with molecular cut off, ion exchange resin columns, reverse osmosis and lyophilizer are avoided.

Another objective is to produce SAMe disulfate monotosylate salt with total impurities not exceeding 2–3% and to develop a process for methylation wherein all the solvents required in the methylation are recyclable to make the process more ecofriendly and economical.

DETAILED DESCRIPTION OF THE INVENTION

Accordingly, the invention provides a method for the production of SAMe, said process comprising the steps of:
a) producing 5'-chloromethyl adenosine hydrochloride by reacting adenosine with thionyl chloride and pyridine at a temperature in the range of 30–35° C.,
b) producing L-homocysteine by treating L-methionine with sodium metal in the presence of water and liquid ammonia at −30 to −40° C.,
c) condensing 5'-chloromethyl adenosine hydrochloride with L-homocysteine in the presence of water and potassium iodide at 70 to 80° C. to obtain S-adenosyl-L-homocysteine (SAH), and purification by acid-base technique and
d) subjecting SAH to methylation using trimethyloxonium tetrafluoroborate (TMOTFB) as a methylating agent in the presence of trifluoroacetic acid (TFA) as a solvent to obtain pure S-adenosyl-L-methionine enriched with (S,S)-isomer in the ratio of 60 to 65%.

In an embodiment, adenosine was suspended in acetonitrile and treated with thionyl chloride at 0 to 5° C. Pyridine was added and the reaction was stirred for few hours at 30–35° C. The reaction was monitored by HPLC. Water was added into the reaction mixture and neutralized with ammonia. The product 5'-chloromethyl adenosine hydrochloride was filtered, washed with chilled water and wet cake used as such for the condensation.

L-Methionine was added to a mixture of water and liquid ammonia at −30 to −40° C. Sodium metal was added maintaining the above temperature and the reaction was monitored by TLC. Ammonia was evaporated and recycled in the process. The aqueous solution of L-homocysteine from the reactor was unloaded and used as such for the condensation with 5'-chloromethyl adenosine hydrochloride.

SAH (S-adenosyl-L-homocysteine) was obtained by the condensation of 5'-chloromethyl adenosine hydrochloride with L-homocysteine in water at 70–80° C. in presence of potassium iodide. The reaction was monitored by HPLC. The product was isolated by precipitation and purified by dissolving in water containing hydrochloric acid and reprecipitated by ammonia solution.

As mentioned in the prior art section, S-adenosyl-L-methionine was conventionally produced by fermentation. Attempts directed to the manufacture of S-adenosyl-L-methionine by chemical methods did not meet with success as the (R,S)-isomer predominated the reaction and it was not possible to obtain the desired (S,S)-isomer in large proportion.

The Applicant during their study found that the production of counterions in the reaction of the prior art processes could be responsible for tipping the balance in favour of (R,S)-isomer. Therefore, in order to overcome this specific drawback in the prior art, the Applicant tried various methylating agents. The Applicant found that the use of a non-linear methylating agent capable of producing a bulky counterion could be one of the factors that could aid the enrichment of (S,S)-isomer in the final product.

Accordingly, the applicant subjected SAH to methylation using as an example, TMOTFB as the methylating agent in the presence of TFA as the exemplary solvent. The end product of this reaction, i.e., SAMe was surprisingly obtained with (S,S)-isomer enrichment of 60 to 65%. The Applicant believes that when SAH is reacted with methylating agent which is non-linear and is capable of producing bulky counterions, sulphonium ions are formed with enrichment of (S,S)-isomer wherein dimethyl ether escapes as a gas, and the bulky tetrafluoroborate counterions generated during the reaction binds with the molecule specifically and directs the incoming methyl group from the required direction, ultimately enriching the end product with (S,S)-isomer.

Another notable feature of the invention is that TMOTFB has not been used in the prior art for any stereoselective methylating reactions and further not used for the methylation of SAH, hence, the process of the invention avoids the use of any chiral reagents.

Accordingly in the present invention, in step (d), SAH is dissolved in a mixture of halogenated aliphatic carboxylic acids or halogenated aromatic carboxylic acids or aliphatic or aromatic sulphonic acids and inorganic acids at −50 to +80° C., more particularly at −20 to +20° C. to obtain SAMe.

While any inorganic acids may be used, the preferred inorganic acids are selected from HBr, HCl, HF, $H_2SO_4$, $HClO_4$ and $H_3PO_4$. Further, the step of methylation is conducted in the presence of carboxylic acids which may be selected from the group comprising trichloroacetic acid, tribromoacetic acid, dichlorobromoacetic acid, dichlorofluoroacetic acid, trifluoroacetic acid, and pentachloropropionic acid, etc. Similarly, the halogenated aromatic carboxylic acids are selected from the group comprising pentachlorobenzoic acid, trichlorodifluorobenzoic acid, pentabromobenzoic acid, etc. In an analogous manner, the halogenated aliphatic sulphonic acids are selected from the group consisting of trifluoromethane sulphonic acid, tribromomethane sulphonic acid, dichlorobromomethane sulphonic acid, dichlorofluoromethane sulphonic acid, trifluoromethane sulphonic acid, and pentachloropropane sulphonic acid, etc.

As said earlier, the methylating agent to be used should be non-linear and capable of producing bulky counterion. Such methylating agents may be selected for example, from the group comprising trimethyloxonium tetrafluoroborate, trimethyloxonium p-toluenesulfonate, trimethyloxonium alkane/aryl sulfonate, trimethyloxonium hexafluorophosphate, trimethyloxonium hexafluoroantimonate, dimethoxycarbenium tetrafluoroborate, O-methyldibenzofuranium tetrafluroborate, etc.

It is also the finding of the Applicant that the use of a methylating agent as suggested above with strong acids such as sulphuric acid, phosphoric acid and trifluoroacetic acid, when used separately or in combination, is capable of enriching the production of (S,S)-isomer to the extent of 60 to 65%.

The progress of methylation reaction is monitored by HPLC. Immediately after the reaction is over, the reaction mixture was distilled under vacuum to remove the volatile components. The reaction mass was quenched into a diluted mineral acid at −10 to +45° C., more particularly at −5 to +25° C., and an organic solvent selected from acetone, ethyl methyl ketone, ethyl isopropyl ketone, methanol, isopropyl alcohol, DMAc, DMSO, DMF, ACN, etc. was added wherein the product precipitated out.

The product was filtered under inert atmosphere and again dissolved in 1–10 volumes of water, more particularly at 2–3 volumes of water at −10 to +45° C., more particularly at −5 to +25° C. and an organic solvent as mentioned above was added and the product precipitated out. The product was filtered under inert atmosphere and dissolved in water and washed 2 times with chlorinated solvent such as chloroform, dichloromethane, dichloroethane, chlorobenzene, etc., to remove impurities.

The product filtration, its redissolution in water and the washing with the said solvent was repeated to get the required quality. Finally, to the aqueous solution containing SAMe, required quantity of sulphuric acid and p-toluene sulfonic acid were added and the solution was spray-dried to get SAMe mixed salt enriched with (S,S)-isomer.

A very important aspect of the invention is the step of diastereoselective methylation wherein TMOTFB and TFA are used as methylating agent and solvent, respectively. The Applicant has found that it is this combination that has succeeded in achieving (S,S)-isomer enrichment to the extent of 60 to 65% which is not reported in the prior art.

Some of the advantages of the invention and the salient features are:

1) it describes the large scale manufacturing of SAH, wherein the process of product purification by acid-base treatment is unique and convenient;
2) trimethyloxonium tetrafluoroborate (TMOTFB) is used first time to stereoselectively methylate SAH;
3) the process of stereoselective methylation is simple and straightforward and can be implemented on manufacturing scale smoothly;
4) since these oxonium compounds are water-soluble, non-volatile, crystalline solids which are rapidly solvolysed in aqueous solution, any danger associated with such alkylating agents are therefore greatly minimized;
5) it does not require any biological source for enzyme or yeast, and affords consistent isomer ratio; and
6) use of trifluoroacetic acid (TFA) as a solvent for methylation is also employed first time and the Applicant has observed that the combination of TMOTFB and TFA only gives the required enrichment during methylation and suppresses impurity formation.

The invention is further illustrated by the following examples which should not be construed as limitations on the inventive scope embodied herein.

EXAMPLE 1

Preparation of 5'-Chloromethyl Adenosine Hydrochloride

Adenosine (100 Kg) was suspended in acetonitrile (350 Lit) and cooled to 0° C. Thionyl chloride (82.5 Lit) was slowly added in 60 min controlling the reaction temperature at 5° C. The reaction mixture was stirred at 5° C. for 4 h. The temperature was allowed to raise to 30–35° C. and maintained at this temperature for 15 h. The reaction was monitored by HPLC and thereafter cooled to 10° C. DM water (900 Lit) was added and the pH was adjusted to 9.5 using 15% ammonia solution (950 Lit). The reaction mass was cooled to 5° C. and stirred for 2 h. The product was filtered and washed with chilled water (300 Lit). Wet cake was dried under vacuum at 40° C.

Yield: 100 Kg

HPLC purity: 99.5%

EXAMPLE 2

Preparation of L-Homocysteine Sodium Salt

To DM water (400 Lit), liquid ammonia (4.5 Kl) was charged and the mixture was cooled to −40° C. To this L-methionine (100 Kg) was charged. Sodium metal pieces (80 Kg) were slowly charged into the above mixture in 2.5 h, while controlling the reaction temperature at −35 to −40° C. The progress of the reaction was monitored by HPLC. Liquid ammonia was evaporated, compressed and stored for recycling. DM water (400 Lit) was charged and the solution was used as such for next reaction. The total weight of the solution was about 850 Kg.

EXAMPLE 3

Preparation of S-Adenosyl-L-Homocysteine

L-Homocysteine sodium salt solution (850 Kg), prepared as described above, was cooled to 10° C. and dil.hydrochloric acid (1:1; 100 Lit) was added til the pH became 11.3 to 11.5. To this solution, 5'-Chloromethyl adenosine hydrochloride (135 Kg) and potassium iodide (13.5 Kg) were added and stirred at 70–80° C. for 5 h. The reaction was monitored by HPLC and cooled to 15° C. Dil.hydrochloric acid (1:1; 200 Lit) was added to bring down the pH to 2.0. Activated carbon (10 Kg) was added, stirred for 30 min and filtered. To the mother liquor, ammonia solution (15%) was added to set the pH to 6.0–6.2. The precipitate was stirred at 20° C. for 24 h and filtered. The solid was washed two times with water (200 Lit). The wet cake was dried at 40° C. under vacuum.

Yield: 135 Kg

HPLC purity: 99.5%

EXAMPLE 4

Improved Preparation of Trimethyloxonium Tetrafluoroborate

Dichloromethane (1.01 Lit) was cooled to −35 to −30° C. Dimethyl ether gas (288.5 g) and boron trifluoride gas (282.7 g) were absorbed into it. Epichlorohydrin (461.5 g) was added in 30–45 min at −5 to −20° C. The temperature was slowly raised to 25° C. in 60 min and maintained for 120 min. The product was filtered and washed with dichloromethane twice with 290 ml each. The solid was transferred to a flask, dichloromethane (1.85 Lit) was added and stirred for 15 min, filtered and washed with dichloromethane twice (2×450 ml). The product was dried under vacuum and under dry nitrogen at 25 to 30° C. and stored below 0° C.

Yield=450 g

Assay=>99.0%

EXAMPLE 5

Preparation of S-Adenosyl-L-Methionine Disulfate Monotosylate

S-Adenosyl-L-homocysteine (1 Kg) was dissolved in trifluoroacetic acid (9.0 Lit) and cooled to −10±2° C. To the solution, conc.sulphuric acid (0.4 Lit) was added. Trimethyloxonium tetrafluoroborate (0.45 Kg) was added in lots over a period of 1 h at −10±2° C. and maintained at this temperature for 3.5 h. The temperature was again raised to −5 to 0° C. and maintained for 2 h. The reaction sample was drawn, diluted with mobile phase and analyzed by HPLC using following condition:

Column=YMC-ODS-A, 4.6 mm×25 cm, C-18, 5 micron.

Buffer=A mixture of 0.02 M citric acid and 0.01 M sodium dihydrogen orthophosphate.

Mobile phase=0.4% w/v Sodium lauryl sulfate in a mixture of 56 volumes of buffer and 44 volumes of acetonitrile.

Detector=UV at 254 nm wavelength

Flow rate=1.5 ml per min.

Column temperature=25° C.

Retention time for (R,S)-isomer=11.6 min and for (S,S)-isomer=12.2 min.

Figure 3:
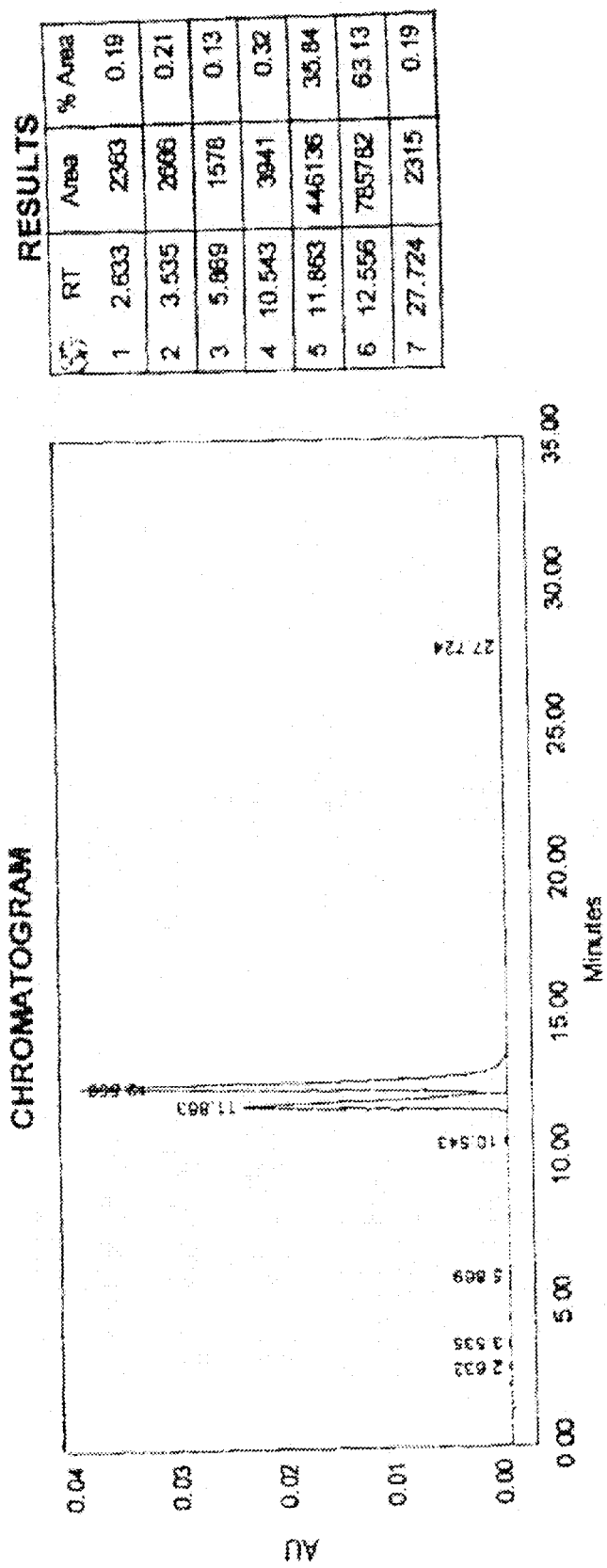
FIG. 3 is a chromatogram showing production of isomers of SAMe by the process of the invention.

The absence of S-adenosyl-L-homocysteine was confirmed. The solvent was removed under vacuum at <30° C. until a residue was obtained. Into the residue, chilled dil. sulphuric acid (6%; 2.0 Lit) was added. Methanol (10.0 Lit) was added and the precipitated product was filtered under nitrogen. Alternatively the reaction mass was quenched in acetone or methanol (15.0 Lit) and the precipitated SAMe sulfate solid was filtered. The filterate containing trifluoroacetic acid and acetone (or methanol) was neutralized using 40% sodium hydroxide and the precipitated sodium fluoride was filtered and neutralized by known methods to recover and recycle trifluoroacetic acid. The filtered SAMe sulfate solid was washed with acetone (2×5.0 Lit) and dissolved in water (2.0 Lit) at 0–5° C. and methanol (10.0 Lit) was added. The precipitate obtained was filtered under nitrogen. The solid was dissolved in DM water (2.0 Lit) at 0–5° C. and washed with dichloromethane (2×5.0 Lit) at the same temperature. The solution was degassed for 30 min and quantified for the content of sulphate. To the solution, required amount of dil.sulphuric acid and p-toluene sulfonic acid were added. The solution was spray-dried with hot air at 140–160° C. to get the required mixed salt of SAMe with enrichment of (S,S)-isomer, as shown in FIG. 3. The first peak in FIG. 3 represents (R,S)-isomer with a retention time of 11.6 min, while the second one represents (S,S)-isomer with a retention time of 12.2 min. This HPLC chart shown in FIG. 3 is comparable and close to the chart depicted in FIG. 1.

Yield=1.4 to 1.6 Kg

HPLC Purity=97.5 to 98.0%

Total Impurities=2.0 to 2.5%

Isomer enrichment [(S,S)-isomer]=61 to 64%

EXAMPLE 6

In situ Preparation of Trimethyloxonium Tetrafluoroborate and its Use in Methylation Dichloromethane (1.01 Lit) was cooled to −35 to −30° C. Dimethyl ether gas (288.5 g) and boron trifluoride gas (282.7 g) were absorbed into it. Epichlorohydrin (461.5 g) was added in 30–45 min at −5 to −20° C. The temperature was slowly raised to 25° C. in 60 min and maintained for 120 min. Thereafter, the solvent was evaporated under vacuum below 30° C. and used as such in situ for methylation of SAH.

To the above mass, a cold mixture (−10 to −20° C.) of S-adenosyl-L-homocysteine (1.0 Kg), trifluoroacetic acid (9.0 Lit) and conc.sulphuric acid (0.4 Lit) was added and stirred for 2 to 3 h. The temperature was raised to −5 to 0° C. and maintained for 2 h. The reaction sample was drawn, diluted with mobile phase and analyzed by HPLC using following condition:

Column=YMC-ODS-A, 4.6 mm×25 cm, C-18, 5 micron

Buffer=A mixture of 0.02 M citric acid and 0.01 M sodium dihydrogen orthophosphate Mobile phase=0.4% w/v Sodium lauryl sulfate in a mixture of 56 volumes of buffer and 44 volumes of acetonitrile Detector=UV at 254 nm wavelength Flow rate=1.5 ml per min.

Column temperature=25° C.

Retention time for (R,S)-isomer=11.6 min and for (S,S)-isomer=12.2 min.

The absence of S-adenosyl-L-homocysteine was confirmed. The solvent was removed under vacuum at <30° C. until a residue was obtained. Into the residue, chilled dil. sulphuric acid (6%; 2.0 Lit) was added. Methanol (10.0 Lit) was added and the precipitated product was filtered under nitrogen. Alternatively the reaction mass was quenched in acetone or methanol (15.0 Lit) and the precipitated SAMe sulfate solid was filtered. The filterate containing trifluoroacetic acid and acetone (or methanol) was neutralized using 40% sodium hydroxide and the precipitated sodium fluoride was filtered and neutralized by known methods to recover and recycle trifluoroacetic acid. The filtered SAMe sulfate solid was washed with acetone (2×5.0 Lit) and dissolved in water (2.0 Lit) at 0–5° C. and methanol (10.0 Lit) was added. The precipitate obtained was filtered under nitrogen. The solid was dissolved in water (2.0 Lit) at 0–5° C. and washed with dichloromethane (3×5.0 Lit) at the same temperature. The solution was degassed for 30 min and quantified for the content of sulphate. To the solution, required amount of dil.sulphuric acid and p-toluene sulfonic acid were added. The solution was spray-dried with hot air at 140–160° C. to get the required mixed salt of SAMe with enrichment of (S,S)-isomer.

Yield=1.2 to 1.3 Kg

HPLC Purity=97.5 to 98.0%

Total impurities=2.0 to 2.5%

Isomer enrichment=(S,S)-isomer=60 to 62%

EXAMPLE 7

Preparation of S-Adenosyl-L-methionine Disulfate Monotosylate

S-Adenosyl-L-homocysteine (1 Kg) was dissolved in trifluoroacetic acid (9.0 Lit) and cooled to −10±2° C. To the solution, conc.phosphoric acid (0.4 Lit, 98%) was added. Trimethyloxonium tetrafluoroborate (0.45 Kg) was added in 1 h and maintained at this temperature for 3.5 h. The temperature was again raised to −5 to 0° C. and maintained for 2 h. The reaction sample was drawn, diluted with mobile phase and analyzed by HPLC using following condition:

Column=YMC-ODS-A, 4.6 mm×25 cm, C-18, 5 micron.
Buffer=A mixture of 0.02 M citric acid and 0.01 M sodium dihydrogen orthophosphate.
Mobile phase=0.4% w/v Sodium lauryl sulfate in a mixture of 56 volumes of buffer and 44 volumes of acetonitrile.
Detector=UV at 254 nm wavelength.
Flow rate=1.5 ml per min.
Column temperature=25° C.
Retention time for (R,S)-isomer=11.6 min and for (S,S)-isomer=12.2 min.

The absence of S-adenosyl-L-homocysteine was confirmed. The solvent was removed under vacuum at <30° C. until a residue was obtained. Into the residue, chilled dil.sulphuric acid (6%; 2.0 Lit) was added. Methanol (10.0 Lit) was added and the precipitated product was filtered under nitrogen. Alternatively the reaction mass was quenched in acetone or methanol (15.0 Lit) and the precipitated SAMe sulfate solid was filtered. The filterate containing trifluoroacetic acid and acetone or methanol was neutralized using 40% sodium hydroxide and the precipitated sodium fluoride was filtered and neutralized by known methods to recover and recycle trifluoroacetic acid. The filtered SAMe sulfate solid was dissolved in water (2.0 Lit) at 0–5° C. and methanol (10.0 Lit) was added. The precipitate obtained was filtered under nitrogen. The solid was dissolved in water (2.0 Lit) at 0–5° C. and washed with dichloromethane (2×5.0 Lit) at the same temperature. The solution was degassed for 30 min and quantified for sulphate content. To the solution, required amount of dil.sulphuric acid and p-toluene sulfonic acid were added. The solution was spray-dried with hot air at 140–160° C. to get the required mixed salt of SAMe with enrichment of (S,S)-isomer.

Yield=1.35 to 1.41 Kg
HPLC Purity=97.5 to 98.0%
Total impurities=2 to 2.5%
Isomer enrichment=(S,S)-isomer=60 to 64%

What is claimed is:

1. A method for the production of a mixture of isomers comprising S-adenosyl-L-methionine (SAMe), said process comprising:
(a) producing 5'-chloromethyl adenosine hydrochloride by reacting adenosine with thionyl chloride and pyridine at a temperature in the range of 30–35° C.,
(b) producing L-homocysteine by treating L-methionine with sodium metal in the presence of water and liquid ammonia at −30 to −40° C.,
(c) condensing 5'-chloromethyl adenosine hydrochloride with L-homocysteine in the presence of water and potassium iodide at 70 to 80° C. to obtain S-adenosyl-L-homocysteine (SAH), purifying the product by acid-base technique, and
(d) subjecting SAil to methylation using a methylating agent selected from the group consisting of trimethyloxonium tetrafluoroborate (TMOTFB), trimethyloxonium p-toluenesulfonate, trimethyloxonium hexafluorophosphate, trimethyloxonium hexafluoroantimonate, trimethyloxonium alkane/aryl sulfonate, dimethoxycarbenium tetrafluoroborate and O-methyldibenzofuranium tetrafluoroborate in the presence of a solvent to obtain a mixture of isomers comprising 60% to 65% e.e. of S-adenosyl-L-methionine.

2. A method as claimed in claim 1, wherein the S-adenosyl-L-homocysteine (SAH) obtained in step (c) is isolated by precipitation and purified by dissolving in water in hydrochloric acid and reprecipitated by ammonia solution.

3. A method as claimed in claim 1, wherein the ratio of SAH: methylating agent is 1:0.4 to 1 w/w.

4. A method as claimed in claim 1, the method further comprising the preparation of a pharmaceutically acceptable salt using the S-adenosyl-L-methionine.

5. A method as claimed in claim 1, wherein the methylation is effected at a temperature in the range of −50° C. to +80° C.

6. A method as claimed in claim 5, wherein the methylation is effected at −20° C. to +20° C.

7. A method as claimed in claim 1, wherein the solvent used in step (d) is selected from the group consisting of a halogenated aliphatic carboxylic acid, a halogenated aromatic carboxylic acid, a halogenated aliphatic acid, a halogenated aromatic sulphonic acid, an inorganic acid and mixtures thereof.

8. A method as claimed in claim 7, wherein the halogenated aliphatic sulphonic acid is selected from the group consisting of trifluoromethane sulphonic acid, tribromomethane sulphonic acid, dichlorobromomethane sulphonic acid, dichlorofluoromethane sulphonic acid, trifluoromethane sulphonic acid, and pentachloropropane sulphonic acid.

9. A method as claimed in claim 7, wherein the halogenated aromatic sulphonic acid is selected from the group consisting of pentachlorobenzene sulphonic acid, trichlorodifluorobenzene sulphonic acid, and pentabromobenzene sulphonic acid.

10. A method as claimed in claim 7, wherein the halogenated aromatic carboxylic acid is selected from the group consisting of pentachlorobenzoic acid, and trichlorodifluorobenzoic acid.

11. A method as claimed in claim 7, wherein the inorganic acid is selected from the group consisting of HBr, HCl, HF, $H_2SO_4$, $HClO_4$, and $H_3PO_4$.

12. A method as claimed in claim 7, wherein the halogenated aliphatic carboxylic acid is selected from the group consisting of trichloroacetic acid, tribromoacetic acid, dichlorobromoacetic acid, dichlorofluoroacetic acid, trifluoroacetic acid and pentachloropropionic acid.

13. A method as claimed in claim 12, wherein the halogenated carboxylic acid is trifluoroacetic acid.

14. A method for the production of S-adenosyl-L-methionine (SAMe), said process comprising:
(a) producing S-adenosyl-L-homocysteine (SAH) by conventional methods, and
(b) subjecting SAH to methylation using a methylating agent selected from the group consisting of trimethyloxonium tetrafluoroborate (TMOTFB), trimethyloxonium p-toluenesulfonate, trimethyloxonium hexafluorophosphate, trimethyloxonium hexafluoroantimonate, trimethyloxonium alkane/aryl sulfonate, dimethoxycarbenium tetrafluoroborate and O-methyldibenzofuranium tetrafluoroborate in the presence of trifluroacetic acid as a solvent to obtain S-adenosyl-L-methionine having a molar ratio (S,S):(R,S) of between 60:40 and 65:35.

15. A method as claimed in claim 14, wherein the SAH is produced by a method comprising: (a) producing 5'-chloromethyl adenosine hydrochloride by reacting adenosine with thionyl chloride and pyridine at a temperature in the range of 30–35° C.; (b) producing L-homocysteine by treating L-methionine with sodium metal in the presence of water and liquid ammonia at −30° C. to −40° C.; and (c) condensing 5'-chloromethyl adenosine hydrochloride with L-homocysteine in the presence of water and potassium iodide at 70 to 8020 C. to obtain S-adenosyl-L-homocysteine (SAH).

16. A method as claimed in claim 14, the method further comprising the preparation of a pharmaceutically acceptable salt using the S-adenosyl-L-methionine.

* * * * *